United States Patent [19]
Muraoka et al.

[11] Patent Number: 5,876,745
[45] Date of Patent: Mar. 2, 1999

[54] METHOD FOR PREPARING A MEDICAL ADHESIVE SHEET

[75] Inventors: Takateru Muraoka; Takashi Kinoshita; Hitoshi Akemi; Saburo Otsuka, all of Osaka, Japan

[73] Assignee: Nitto Denko Corporation, Osaka, Japan

[21] Appl. No.: 742,487

[22] Filed: Jan. 23, 1997

Related U.S. Application Data

[63] Continuation of Ser. No. 296,427, Aug. 26, 1994.

[30] Foreign Application Priority Data

Aug. 27, 1993 [JP] Japan ................................ 5-212840
Aug. 27, 1993 [JP] Japan ................................ 5-212841

[51] Int. Cl.$^6$ ........................................................ A61K 9/70
[52] U.S. Cl. ............................................ 424/448; 424/443
[58] Field of Search .................................... 424/445, 448

[56] References Cited

U.S. PATENT DOCUMENTS

| | | | |
|---|---|---|---|
| 4,719,226 | 1/1988 | Otsuka | 514/449 |
| 4,784,653 | 11/1988 | Bolton et al. | 604/307 |
| 4,938,964 | 7/1990 | Sakai | 424/443 |
| 5,298,258 | 3/1994 | Akemi et al. | 424/484 |
| 5,374,429 | 12/1994 | Kinoshita | 424/448 |

FOREIGN PATENT DOCUMENTS

| | | |
|---|---|---|
| A-0304536 | 3/1989 | European Pat. Off. |
| 2212419 | 8/1990 | European Pat. Off. |
| 435199 | 7/1991 | European Pat. Off. |
| A-0-531938 | 3/1993 | European Pat. Off. |
| A-0569862 | 11/1993 | European Pat. Off. |

*Primary Examiner*—Thurman K. Page
*Assistant Examiner*—G. Brouillette
*Attorney, Agent, or Firm*—Sughrue, Mion, Zinn, Macpeak & Seas, PLLC

[57] ABSTRACT

A medical adhesive sheet comprising a support having a laminate structure comprising a non-porous sheet and a porous sheet, and a pressure-sensitive layer comprising an acrylic polymer prepared by polymerizing an alkyl (meth) acrylate as a main component monomer, and an organic liquid component which is compatible with the acrylic polymer, formed on the porous sheet side of the support, the layer being subjected to a crosslinking treatment, wherein the pressure-sensitive adhesive layer is embedded in the porous sheet, reaching the laminate interface between the non-porous sheet and the porous sheet. The medical adhesive sheet has improved anchoring property of its pressure-sensitive adhesive layer to the support while exhibiting a good balance between adhesion to the skin and low irritation to the skin.

16 Claims, 1 Drawing Sheet

FIGURE
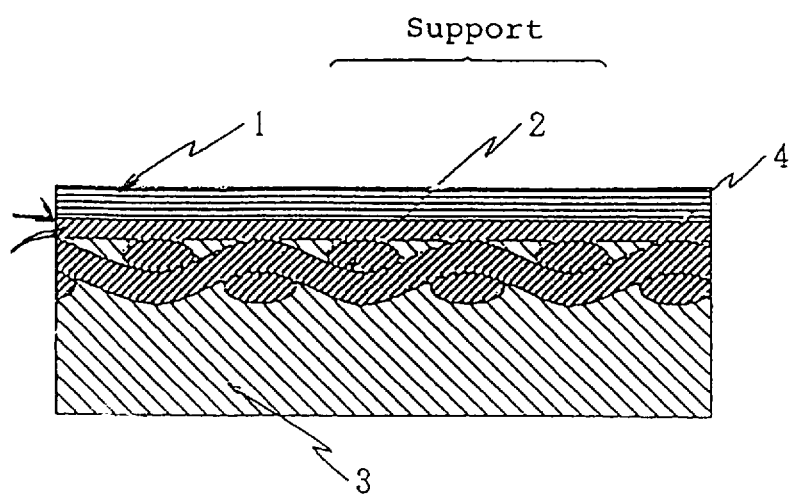

METHOD FOR PREPARING A MEDICAL ADHESIVE SHEET

This is a continuation of application Ser. No. 08/296,427 filed Aug. 26, 1994.

FIELD OF THE INVENTION

This invention relates to medical adhesive sheet which can be adhered to a skin for protection of the skin or for continuous administration of a drug for percutaneous absorption into a living body to treat or prevent various diseases.

BACKGROUND OF THE INVENTION

Various types of so-called adhesive tape-like medical adhesive sheets comprising a support such as a nonwoven sheet, a plastic film or the like having formed on one surface thereof a pressure-sensitive adhesive layer have been proposed as dressings for protection of the affected part of the skin or for administration of a drug for treating a disease or for prevention through a skin surface.

It is required for those medical adhesive sheets to have adhesiveness to the skin to some extent to prevent the same from falling off the skin surface to which the sheet is applied. However, physical irritation increases in peeling and removing the sheet from the skin surface as the adhesiveness to the skin increases, and pain or peeling of stratum corneum tends to occur. As a result, there is the possibility to give unnecessary irritation or damage to the skin surface, thereby giving pain to the user.

It is therefore necessary to appropriately decrease the adhesiveness to the skin in relationship with decrease of the skin irritation, and the adhesiveness to the skin is sacrificed to a certain degree, or the insufficient adhesiveness to the skin is supplemented by covering with a separately prepared adhesive sheet.

The medical adhesive sheet is also required to have, besides the appropriate adhesiveness, cohesiveness of the adhesive layer and an anchoring property of the adhesive layer to the support for preventing the adhesive from remaining on the skin on removal (adhesive remaining phenomenon). In particular, where the adhesive layer contains a drug for percutaneous absorption, the drug should have stability with time (insusceptibility to decomposition) in the adhesive layer and releasability from that layer (percutaneous absorbability). Thus, development of medical adhesive sheets must be undertaken with due consideration for these various factors.

The present inventors had been devoted to develop a low-irritating medical adhesive sheet, especially an adhesive sheet having an adhesive layer comprising an acrylic polymer, which has hitherto been used as an adhesive less irritating to the skin, endowed with increased softness by incorporating a relatively large amount of an organic liquid component having a plasticizing action. As a result, they succeeded to obtain an adhesive layer with good balance between skin adhesion and low skin irritation. However, where the support, on which such an adhesive layer is laminated, is a mere plastic film or a composite film composed of a plastic film and a porous film, cases are sometimes met with, in which the proportions of the components constituting the adhesive layer vary and, in particular, the organic liquid component in the adhesive layer blooms to the interface between the support and the adhesive layer, failing to exert sufficient anchoring force. Such being the case, it turned out that anchoring failure tends to occur on removal from the skin after use, allowing the adhesive to remain on the skin. Improvement on anchoring property in medical adhesive sheets is of extreme importance to be considered in the development of medical adhesive sheets, although little study has ever been directed thereto.

SUMMARY OF THE INVENTION

As a result of further investigation, the present inventors have found that an adhesive layer mainly comprising an acrylic polymer and a relatively large amount of a plasticizing organic liquid component can be made to exert an excellent anchoring property to a support by creating a specific state on the interface between the support and the adhesive layer. The present invention has been reached by this finding.

The present invention provides a medical adhesive sheet comprising a support having a laminate structure comprising a non-porous sheet and a porous-sheet, and a pressure-sensitive adhesive layer comprising an acrylic polymer prepared by polymerizing an alkyl (meth)acrylate as a main component monomer, and an organic liquid component which is compatible with the acrylic polymer, formed on the porous sheet side of the support, the layer being subjected to a crosslinking treatment, wherein the pressure-sensitive adhesive layer is embedded in the porous sheet, reaching the laminate interface between the non-porous sheet and the porous sheet.

The present invention also provides a medical adhesive sheet whose pressure-sensitive adhesive layer contains a drug for percutaneous absorption, especially a drug having a systemic action.

BRIEF DESCRIPTION OF THE DRAWING

The Figure is a cross section of a medical adhesive sheet according to the present invention, in which woven fabric is used as a porous sheet of the support.

DETAILED DESCRIPTION OF THE INVENTION

The pressure-sensitive adhesive layer in the medical adhesive sheet according to the present invention is a layer obtained by crosslinking a composition comprising an acrylic polymer obtained by polymerizing an alkyl (meth) acrylate as a main component monomer, and an organic liquid component compatible with the acrylic polymer. If the acrylic polymer is replaced with other polymeric materials or polymers, such as natural rubber, various synthetic rubbers and silicone resins, there is a tendency that the organic liquid component present in a relatively large proportion could not be retained in the pressure-sensitive adhesive layer due to lack of compatibility with these polymeric materials or polymers and would bloom to the surface during storage. Additionally, it is difficult to control the degree of crosslinking of the pressure-sensitive layer containing such polymeric materials or polymers. Where a drug is incorporated into the pressure-sensitive adhesive layer, polymeric materials or polymers other than the acrylic polymers are hardly useful because some drugs are given only a limited choice of the polymer matrix to be combined with, taking releasability or stability of the drug into consideration.

The alkyl (meth)acrylates which can be used as a main component monomer to obtain the above-described acrylic polymer include those having from 4 to 18 carbon atoms in the alkyl moiety thereof, such as butyl (meth)acrylate, pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate, and tridecyl (meth)acrylate. The alkyl moiety may be either a straight-chain alkyl group or a branched alkyl group. These alkyl (meth)acrylates are used, either individually or in combination of two or more thereof, in a proportion of at least 40% by weight, preferably 50 to 98% by weight, and still preferably from 60 to 98% by weight, based on the total monomers. If desired, part of the alkyl (meth)acrylate monomer(s) having 4 to 18 carbon atoms in the alkyl moiety thereof may be replaced with those having a lower alkyl group containing 3 or less carbon atoms, such as methyl (meth)acrylate, ethyl (meth)acrylate, and propyl (meth)acrylate.

The acrylic polymer used in the present invention may be a copolymer obtained by copolymerizing the above-described alkyl (meth)acrylate monomer and a copolymerizable monomer, such as a polar monomer and/or a vinyl monomer.

Examples of suitable polar monomers include carboxyl-containing monomers, such as (meth)acrylic acid, itaconic acid, maleic acid, maleic anhydride, and crotonic acid; sulfoxy-containing monomers, such as styrenesulfonic acid, allylsulfonic acid, sulfopropyl (meth)acrylate, (meth)acryloyloxynaphthalenesulfonic acid, and acrylamidomethylpropanesulfonic acid; hydroxyl-containing monomers, such as hydroxyethyl (meth)acrylate and hydroxypropyl (meth)acrylate; amido-containing monomers, such as (meth)acrylamide, dimethyl(meth)acrylamide, N-butylacrylamide, N-methylol(meth)acrylamide, and N-methylolpropane (meth)acrylamide; alkylaminoalkyl-containing monomers, such as aminoethyl (meth)acrylate, dimethylaminoethyl (meth)acrylate, and t-butylaminoethyl (meth)acrylate; alkoxyalkyl (meth)acrylates, such as methoxyethyl (meth)acrylate and ethoxyethyl (meth)acrylate; alkoxy-containing (meth)acrylic esters or (meth)acrylic esters containing an oxido bond in the side chain thereof, such as tetrahydrofurfuryl (meth)acrylate, methoxyethylene glycol (meth)acrylate, methoxydiethylene glycol (meth)acrylate, and methoxypolyethylene glycol (meth)acrylate; and (meth)acrylonitrile. These polar comonomers may be used either individually or in combination of two or more thereof.

Examples of suitable vinyl monomers include vinyl esters, such as vinyl acetate and vinyl propionate; and nitrogen-containing heterocyclic vinyl compounds, such as N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam, and vinyloxazole. These vinyl comonomers may be used either individually or in combination of two or more thereof.

Among the above-enumerated polar monomers and vinyl monomers preferred are carboxyl-containing monomers, hydroxyl-containing monomers, amido-containing monomers, alkoxyalkyl (meth)acrylates, alkoxy-containing (meth)acrylic esters, and (meth)acrylic esters containing an oxido bond in the side chain thereof; for they not only have such a functional group to become an active site in the subsequent crosslinking but also are effective to raise the glass transition temperature of an acrylic polymer to improve the cohesive force. From the viewpoint of improvement of a cohesive force and a dissolving power for a drug, if used, it is preferable to use vinyl esters, nitrogen-containing heterocyclic vinyl compounds, and the like.

The proportion of the polar monomer and/or vinyl monomer to be copolymerized can be selected arbitrarily with attention to the cohesive force of the adhesive layer or solubility of a drug, if incorporated. In general, these comonomers are used in a proportion of 60% by weight or less, preferably from 2 to 50% by weight, and more preferably from 2 to 40% by weight, based on the weight of the total monomers.

The organic liquid component which constitutes the pressure-sensitive adhesive layer in combination with the acrylic polymer should be compatible with the acrylic polymer so as to produce an effect of plasticizing the pressure-sensitive adhesive layer. Plasticization of the pressure-sensitive adhesive layer gives a soft feeling to the skin when the adhesive sheet is applied to the skin. This component also serves, upon being subjected to crosslinking, to impart a proper cohesive force to the pressure-sensitive adhesive layer while minimizing the irritation to the skin on removal.

For the organic liquid component to exert these effects, it is preferably used in an amount of from 25 to 200 parts by weight, preferably from 40 to 180 parts by weight, and more preferably from 60 to 180 parts by weight, per 100 parts by weight of the acrylic polymer. If used in too low an amount, the organic liquid component does not manifest its plasticizing effect sufficiently for significant reduction of skin irritation. If used in too high an amount, on the other hand, the pressure-sensitive adhesive layer would be plasticized excessively, resulting in reduction in cohesive force. It follows that the pressure-sensitive adhesive tends to remain on the skin on peeling and to cause increased skin irritation.

The organic liquid component which can be used in the present invention is liquid at room temperature and compatible with the above-described acrylic copolymer. Specific examples include glycols, such as ethylene glycol, diethylene glycol, triethylene glycol, propylene glycol, polyethylene glycol, and polypropylene glycol; fats and oils, such as olive oil, castor oil, squalene, and lanolin; organic solvents, such as ethyl acetate, ethyl alcohol, dimethyldecyl sulfoxide, methyloctyl sulfoxide, dimethyl sulfoxide, dimethylformamide, dimethylacetamide, dimethyllaurylamine, dodecylpyrrolidone, and isosorbitol; liquid surface active agents; hydrocarbons, such as liquid paraffin; ethoxidized stearyl alcohol, glycerol esters, phthalic esters, isopropyl myristate, isotridecyl myristate, diethyl sebacate, ethyl laurate, N-methylpyrrolidone, ethyl oleate, oleic acid, diisopropyl adipate, isopropyl palmitate, octyl palmitate, and 1,3-butanediol. These organic liquid components may be used either individually or in combination of two or more thereof. From the standpoint of reduction of skin irritation or acceleration of percutaneous absorption of a drug, if used, preferred of them are long chain fatty acid monoalkyl or dialkyl esters, such as isopropyl myristate, diethyl sebacate, octyl palmitate, ethyl oleate, diethyl phthalate, and diisopropyl adipate; fatty acids, such as monocapric acid and oleic acid; and liquid surface active agents, such as sorbitan monocaprylate; and mixtures thereof.

In the present invention, the composition comprising the acrylic polymer and the organic liquid component is subjected to crosslinking in order to increase the internal cohesive force of the pressure-sensitive adhesive layer thereby providing a feeling of moderate softness and moderate adhesion when applied to the skin as well as cohesiveness of the pressure-sensitive adhesive layer. Crosslinking makes the pressure-sensitive adhesive layer such a viscoelastic body with creep characteristics and undergoes no cohesive failure even with an outer shear stress being imposed to the pressure-sensitive adhesive sheet applied to the skin and also exhibits adhesion to the skin.

Crosslinking can be effected by physical crosslinking with radiations, such as ultraviolet rays or electron rays, or chemical crosslinking using a crosslinking agent, such as a polyisocyanate compound, an organic peroxide, an organometallic salt, a metal alcoholate, a metal chelate compound, a melamine derivative, or a polyfunctional compound. In using a radiation or an organic peroxide, some drugs may undergo decomposition. In using a highly reactive isocyanate compound or a metallic or organometallic salt generally used for crosslinking, it sometimes increases the viscosity of the composition to reduce the workability. It is possible to previously incorporate a polyfunctional monomer, such as a diacrylate, as a tackifier into the acrylic polymer. In this case, attention should be brought to the handling properties of the resulting coating composition because some polyfunctional monomers may increase the viscosity of the composition. Accordingly, taking reactivity and handling properties into consideration, preferred of the above-described crosslinking agents are metal alcoholates containing titanium or aluminum, metal chelate compounds, and polyfunctional isocyanates (especially trifunctional isocyanates). These crosslinking agents do not cause an increase in viscosity of the composition during the steps of from coating to drying to ensure extremely excellent workability. They are usually used in an amount of from about 0.05 to 5 parts by weight per 100 parts by weight of the acrylic polymer. Where the acrylic polymer does not have a functional group reactive with the crosslinking agent, it can be converted into a crosslinkable structure by, for example, an alkali treatment prior to the crosslinking treatment.

If desired, the adhesive layer may contain additives, such as antioxidants, pigments, fillers, percutaneous absorption enhancers, stabilizers, drug dissolving assistants, and drug dissolving restrainers, and the like in a total amount of from about 2 to 50 parts by weight per 100 parts by weight of the acrylic polymer.

The medical adhesive sheet having the above-described structure can contain in its pressure-sensitive adhesive layer a drug for percutaneous absorption either in a dissolved state or in a dispersed state to prepare a medical adhesive sheet which can be used for treatment and/or prevention of various diseases.

Drugs which can be incorporated into the adhesive layer include corticosteroids, analgetic antiinflammatory agents, hypnotic sedatives, tranquilizers, antihypertensives, hypotensive diuretics, antibiotics, anesthetics, antimicrobials, antifungals, vitamins, coronary vasodilators, antihistaminics, antitussives, sex hormones, antidepressants, cerebral circulation improving agents, antiemetics, antitumor agents, and biological preparations. If desired, these drugs may be used in combination of two or more thereof. In general, orally administered drugs undergo primary metabolism on the first pass effect through the liver, while injected drugs have a short duration. Accordingly, considering prevention of the first metabolism of a drug and long-lasting maintenance of an effective concentration in blood, those having a systemic action are preferred among the above-described drugs for percutaneous administration.

The content of the drug may be selected appropriately according to the kind of the drug or the purpose of administration and usually ranges from about 1 to 40% by weight, preferably from about 2 to 30% by weight, based on the weight of the adhesive layer. A drug content of less than 1% by weight cannot be expected to release the drug in a level sufficiently effective for the treatment or prevention of a disease. A drug content exceeding 40% by weight not only produces no further increase of the therapeutic or prophylactic effect but is uneconomical.

The medical adhesive sheet of the present invention comprises a support having formed on one side thereof the above-described adhesive layer as shown in the Figure. The support has a laminate structure composed of a non-porous sheet 1 and a porous sheet 2, and a pressure-sensitive adhesive layer 3 is formed on the side of the porous sheet 2 in such a manner that the pressure-sensitive adhesive layer 3 is embedded in the porous sheet 2, reaching the laminate interface between the non-porous sheet 1 and the porous sheet 2. It is desirable for obtaining a practical anchoring effect that the pressure-sensitive adhesive layer should be embedded in the porous sheet to such an extent that, when the non-porous sheet is forcedly detached from the porous sheet at the interface, the pressure-sensitive adhesive layer exposed on the non-porous sheet may have a peel strength of not less than 5 g/24 mm width, preferably not less than 8 g/24 mm width, in a peel test to a Bakelite plate at a rate of pulling of 300 mm/min, as tested in Examples hereinafter given. The terminology "non-porous sheet" as used herein means a sheet which has not been subjected to any positive hole-making treatment, such as perforation or expansion. The terminology "porous sheet" as used herein means a sheet which has been subjected to a positive treatment for making it porous or a sheet having through-pores, such as cloth.

The non-porous sheet which can be used in the present invention includes a sheet of various plastics, such as polyester, nylon, saran, polyethylene, polypropylene, polyvinyl chloride, polyvinylidene chloride, an ethylene-ethyl acrylate copolymer, an ethylene-vinyl acetate copolymer, an ethylene-vinyl alcohol copolymer, polytetrafluoroethylene, Surlyn, polyurethane, rayon, vinylon, acrylic resins, acetate, and triacetate; a metal-deposited plastic sheet, and a metal foil, either singly or in the form of a laminate of two or more of these sheets. Preferred of them are those having so-called non-strike through properties, i.e., impermeability to an organic liquid component or a drug contained in the adhesive layer, such as a sheet of polyester, polytetrafluoroethylene, polyethylene or polypropylene.

The porous sheet which can be used in the present invention includes a sheet obtained by subjecting the above-enumerated non-porous sheet to perforation or expansion to form open cells, a paper, a woven fabric, a nonwoven fabric, and a knitted fabric. A porous sheet comprising a nonwoven fabric or a woven fabric is preferred for sufficient embedment of the adhesive layer. In particular, the nonwoven or woven fabric having a basis weight of from 5 to 30 g/m$^2$, preferably from 8 to 20 g/m$^2$, is recommended for ensuring improved anchoring property of the pressure-sensitive adhesive layer.

The method of laminating the non-porous sheet and the porous sheet is not particularly limited and includes, for example, extrusion laminating, heat bonding under pressure, or lamination using a conventional adhesive, such as a polyester-based adhesive. To ensure lamination so as not to cause delamination at the laminate interface, lamination using an adhesive is preferred. The thickness of the support is not particularly limited. Taking into consideration the softness of the medical adhesive sheet on applying to the skin and the anchoring property between the pressure-sensitive adhesive layer and the porous sheet, it is recommended that the thickness of the non-porous sheet be from about 0.5 to 50 µm, preferably from about 1 to 25 µm, and that of the porous sheet be from about 10 to 500 µm, preferably from about 10 to 200 µm, totaling from about 11 to 550 µm, preferably from about 15 to 225 µm. While the thickness of the pressure-sensitive adhesive sheet is difficult to specify because it is embedded in the porous sheet, it usually ranges from about 30 to 200 µm, preferably from about 40 to 180 µm, and more preferably from 50 to 150 µm, as expressed in terms of a thickness difference between the total thickness of the pressure-sensitive adhesive sheet and the thickness of the support.

The medical adhesive sheet of the present invention is characterized in that the pressure-sensitive adhesive layer is formed on the porous sheet side of the support in such a manner that the pressure-sensitive adhesive layer is embedded in the porous sheet, reaching the laminate interface with the non-porous sheet (or the interface between the porous sheet and an adhesive layer which may be used for laminating the non-porous sheet with the porous sheet, as shown in the Figure, in which numeral 4 indicates an adhesive). The pressure-sensitive adhesive layer can be formed on the surface of the support by a direct coating method in which a solution of the pressure-sensitive adhesive layer-forming components is directly applied to the porous sheet side followed by drying or a transfer coating method comprising applying a solution of the pressure-sensitive adhesive layer-forming components to a separator followed by drying to form a pressure-sensitive adhesive layer and laminating the pressure-sensitive adhesive layer to the porous sheet side of a support under pressure to transfer the pressure-sensitive adhesive layer onto the support. Where the pressure-sensitive adhesive layer has a relatively small cohesive force, the transfer coating suffices to embed the pressure-sensitive adhesive layer in the porous sheet. In order to surely embed the pressure-sensitive adhesive layer in the porous sheet to obtain improved anchoring property, the direct coating method is preferred.

It is desirable to protect the surface of the pressure-sensitive adhesive layer formed on the support with a conventional separator, which is stripped on use. It is also desirable that the medical adhesive sheet should be in sterile packages so as to prevent evaporation loss of an organic liquid component or a drug contained in the pressure-sensitive adhesive layer.

As described above, the medical adhesive sheet according to the present invention comprises a pressure-sensitive adhesive layer containing an acrylic polymer and an organic liquid component and having been subjected to crosslinking, surely embedded in its support having a specific laminate structure. Therefore, it has a satisfactory balance between adhesion to the skin and low irritation to the skin and, in addition, excellent anchoring property between the support and the pressure-sensitive adhesive layer.

The present invention will now be illustrated in greater detail with reference to Examples, but it should be understood that the present invention is not to be construed as being limited thereto. All the percents and parts are by weight unless otherwise indicated.

EXAMPLE 1

72 Parts of 2-ethylhexyl acrylate, 25 parts of N-vinyl-2-pyrrolidone, and 3 parts of acrylic acid were copolymerized in ethyl acetate to prepare an acrylic polymer solution. 50 Parts of the solid content of the acrylic polymer solution was mixed with 50 parts of isopropyl myristate, and to the mixture was added 0.5 part, per 100 parts of the solid content of the acrylic polymer, of aluminum tris(acetylacetonate) as a 1% ethyl acetate solution. Ethyl acetate was further added thereto to prepare a solution having an appropriate viscosity for coating.

Separately, a polyester film having a thickness of 2 µm was extrusion laminated on polyester nonwoven fabric having a basis weight of 12 g/m² to obtain a support.

The above-prepared coating solution was applied to the nonwoven fabric side of the support and dried to form a crosslinked pressure-sensitive adhesive layer having a dry thickness of 80 µm.

A 75 µm thick polyester separator was laminated on the adhesive layer to prepare a medical adhesive sheet.

EXAMPLE 2

55 Parts of the solid content of an acrylic polymer prepared from 97 parts of 2-ethylhexyl acrylate and 3 parts of acrylic acid were mixed with 45 parts of isopropyl myristate, and to the mixture was added 0.5 part of aluminum tris(acetylacetonate) per 100 parts of the solid content of the acrylic polymer to prepare a coating solution.

The coating solution was applied to a 75 µm thick polyester separator and dried to form a crosslinked pressure-sensitive adhesive layer having a dry thickness of 80 µm. The pressure-sensitive adhesive layer on the separator was laminated on the nonwoven fabric side of the same support as used in Example 1 to prepare a medical adhesive sheet.

EXAMPLE 3

A medical adhesive sheet was prepared in the same manner as in Example 1, except for replacing the aluminum tris(acetylacetonate) as a crosslinking agent with 1 part of dipropoxybis(acetylacetonato)titanium.

EXAMPLE 4

A drug-containing medical adhesive sheet was prepared in the same manner as in Example 1, except that the coating solution was prepared by mixing 50 parts of the solid content of the acrylic polymer with 40 parts of isopropyl myristate and 10 parts of Metoprolol and adding to the resulting mixture 0.8 part, per 100 parts of the solid content of the acrylic polymer, of aluminum tris(acetylacetonate).

EXAMPLE 5

A drug-containing medical adhesive sheet was prepared in the same manner as in Example 2, except that the coating solution was prepared by mixing 45 parts of the solid content of the acrylic polymer with 45 parts of isopropyl myristate and 10 parts of Ketoprofen and adding to the resulting mixture 0.3 part, per 100 parts of the solid content of the acrylic polymer, of a trifunctional isocyanate "Coronate HL", produced by Nippon Polyurethane Industry Co., Ltd.

EXAMPLE 6

A medical adhesive sheet was prepared in the same manner as in Example 2, except for replacing isopropyl myristate as an organic liquid component with diethyl sebacate.

EXAMPLE 7

A drug-containing medical adhesive sheet was prepared in the same manner as in Example 4, except for changing the solid content of the acrylic polymer and the amount of isopropyl myristate to 40 parts and 50 parts, respectively.

EXAMPLE 8

A drug-containing medical adhesive sheet was prepared in the same manner as in Example 5, except for replacing 45 parts of isopropyl myristate as an organic liquid component with a combination of 30 parts of isopropyl myristate and 15 parts of diethyl sebacate and increasing the amount of the trifunctional isocyanate to 0.35 part.

EXAMPLE 9

A drug-containing medical adhesive sheet was prepared in the same manner as in Example 4, except for replacing the 40 parts of isopropyl myristate with a combination of 25 parts of isopropyl myristate and 15 parts of diethyl sebacate.

COMPARATIVE EXAMPLE 1

The same coating solution as prepared in Example 1 was applied to a 75 μm thick polyester separator and dried to form a crosslinked pressure-sensitive adhesive layer having a dry thickness of 80 μm.

The thus formed pressure-sensitive adhesive layer was adhered to the nonwoven fabric side of the same support as used in Example 1 to prepare a medical adhesive sheet.

COMPARATIVE EXAMPLE 2

A medical adhesive sheet was prepared in the same manner as in Comparative Example 1, except for using 1 part, per 100 parts of the solid content of the acrylic polymer, of titanium acetoacetonate in place of 0.5 part of aluminum tris(acetylacetonate).

COMPARATIVE EXAMPLE 3

A medical adhesive sheet was prepared in the same manner as in Comparative Example 1, except for replacing isopropyl myristate as an organic liquid component with diethyl sebacate.

COMPARATIVE EXAMPLE 4

A drug-containing medical adhesive sheet was prepared in the same manner as in Example 1, except that the coating solution was prepared by mixing 90 parts of the solid content of the acrylic polymer with 10 parts of Metoprolol and the crosslinking agent was not added thereto. The pressure-sensitive adhesive layer of the resulting adhesive sheet did not contain an organic liquid component and was not crosslinked.

COMPARATIVE EXAMPLE 5

A drug-containing medical adhesive sheet, with the pressure-sensitive adhesive layer thereof not containing an organic liquid component and being not crosslinked, was prepared in the same manner as in Comparative Example 4, except for adding 15 parts of Metoprolol to 85 parts of the solid content of the acrylic polymer.

COMPARATIVE EXAMPLE 6

The same coating solution as prepared in Example 1 was applied to a 25 μm thick, non-porous polyester film and dried to form a crosslinked pressure-sensitive adhesive layer having a dry thickness of 80 μm.

A 75 μm thick polyester separator was laminated on the pressure-sensitive adhesive layer to prepare a medical adhesive sheet.

COMPARATIVE EXAMPLE 7

50 Parts of the solid content of the same acrylic polymer as prepared in Example 1 were mixed with 40 parts of isopropyl myristate and 10 parts of Metoprolol, and to the mixture was added 0.8 part, per 100 parts of the solid content of the acrylic polymer, of aluminum tris(acetylacetonate) to prepare a coating solution. The solution was applied to a 75 μm thick polyester separator and dried to form a crosslinked pressure-sensitive adhesive layer having a dry thickness of 80 μm.

The pressure-sensitive adhesive layer was laminated on the non-woven fabric side of the same support as used in Example 1 to prepare a drug-containing medical adhesive sheet.

COMPARATIVE EXAMPLE 8

A drug-containing medical adhesive sheet was prepared in the same manner as in Comparative Example 7, except for changing the solid content of the acrylic polymer and the amount of isopropyl myristate to 40 parts and 50 parts, respectively.

COMPARATIVE EXAMPLE 9

A drug-containing medical adhesive sheet was prepared in the same manner as in Comparative Example 7, except for replacing 40 parts of isopropyl myristate to 40 parts of diethyl sebacate.

COMPARATIVE EXAMPLE 10

A drug-containing medical adhesive sheet was prepared in the same manner as in Comparative Example 7, except for replacing the 40 parts of isopropyl myristate as an organic liquid component with a combination of 25 parts of isopropyl myristate and 15 parts of diethyl sebacate.

Each of the medical adhesive sheets obtained in the foregoing Examples and Comparative Examples was evaluated in accordance with the following test methods. The results obtained are shown in Table 1 below.

1) Application Test:

A cut piece of the medical adhesive sheet having an area of 5 cm$^2$ (22.5 mm×22.5 mm) was applied to the skin of a human upper arm for 24 hours. For those samples containing a drug for percutaneous absorption, the amount of the drug which had migrated into the skin (hereinafter referred to as drug migration weight) was measured as a difference in drug content before and after the 24 hour application. After the 24 hour application, the medical adhesive sheet was peeled off the skin, and remaining of the adhesive layer on the skin due to anchoring failure was visually observed.

2) Confirmation of Embedment in Porous Sheet:

In order to confirm that the pressure-sensitive adhesive layer was embedded in the porous sheet to reach the laminate interface with the non-porous sheet, the separator was stripped off each sample, and a 12 μm polyester film having not been subjected to a release treatment was laminated on the exposed pressure-sensitive adhesive layer instead.

The resulting sample was cut to a 24 mm wide strip, and only the non-porous sheet was forcedly detached to expose the laminate interface of the porous sheet.

The thus exposed porous sheet side was adhered to a Bakelite plate by giving one stroke of a roller having a load of 300 g. Then, the whole medical adhesive sheet was peeled from the plate at a peel angle of 180° at a rate of pulling of 300 mm/min to measure the peel strength.

TABLE 1

| Example No. | Remaining of Adhesive | Drug Migration Weight (μg) | Peel Strength of Embedded Adhesive Layer (g/24 mm width) |
|---|---|---|---|
| Example 1 | none | — | 16 |
| Example 2 | none | — | 12 |
| Example 3 | none | — | 15 |
| Example 4 | none | 1250 ± 136 | 20 |

TABLE 1-continued

| Example No. | Remaining of Adhesive | Drug Migration Weight (μg) | Peel Strength of Embedded Adhesive Layer (g/24 mm width) |
|---|---|---|---|
| Example 5 | none | 1485 ± 216 | 14 |
| Example 6 | none | — | 10 |
| Example 7 | none | 1528 ± 186 | 19 |
| Example 8 | none | 1427 ± 102 | 13 |
| Example 9 | none | 1218 ± 116 | 18 |
| Comparative Example 1 | observed | — | 2 |
| Comparative Example 2 | observed | — | 1 |
| Comparative Example 3 | observed | — | 2 |
| Comparative Example 4 | none | 596 ± 127 | 5 |
| Comparative Example 5 | none | 836 ± 286 | 4 |
| Coinparative Example 6 | observed | — | — |
| Comparative Example 7 | observed | unmeasurable due to adhesive remaining | 2 |
| Comparative Example 8 | observed | unmeasurable due to adhesive remaining | 1 |
| Comparative Example 9 | observed | unmeasurable due to adhesive remaining | 1 |
| Comparative Example 10 | observed | unmeasurable due to adhesive remaining | 2 |

As is apparent from the results in Table 1, the medical adhesive sheet according to the present invention exhibits moderate adhesion to the skin as well as satisfactory anchoring property between the pressure-sensitive adhesive layer and the support. Where a drug for percutaneous absorption is incorporated into the pressure-sensitive adhesive layer, the pressure-sensitive adhesive layer shows high rate of drug migration to the skin, proving useful for percutaneous administration of the drug. To the contrary, the samples of Comparative Examples 1 to 3 and 7 to 10 were unsatisfactory for practical use in terms of anchoring property and adhesive remaining because the pressure-sensitive adhesive layer was not sufficiently embedded in the porous sheet.

EXAMPLE 10

50 Parts of the solid content of the same acrylic polymer as prepared in Example 1 were mixed with 40 parts of isopropyl myristate and 10 parts of Bunitrolol, and to the mixture was added 1 part, per 100 parts of the solid content of the acrylic polymer, of aluminum tris(acetylacetonate) as a 1% ethyl acetate solution. Ethyl acetate was further added thereto to adjust to an appropriate viscosity for coating to prepare a coating solution.

Separately, a polyester film having a thickness of 2 μm was extrusion laminated on polyester nonwoven fabric having a basis weight of 12 g/m² to obtain a support.

The above-prepared coating solution was applied to the non-woven fabric side of the support and dried to form a crosslinked pressure-sensitive adhesive layer having a dry thickness of 80 μm.

A 75 μm thick polyester separator was laminated onto the pressure-sensitive adhesive layer to prepare a drug-containing medical adhesive sheet.

EXAMPLE 11

A coating solution was prepared in the same manner as in Example 2, except for further adding 10 parts of Bunitrolol per 50 parts of the acrylic polymer and changing the amount of aluminum tris(acetylacetonate) as a crosslinking agent to 0.8 part per 100 parts of the solid content of the acrylic polymer.

The resulting coating solution was applied to a 75 μm thick polyester separator and dried to form a crosslinked pressure-sensitive adhesive layer having a dry thickness of 80 μm.

The pressure-sensitive adhesive layer was laminated onto the non-woven fabric side of the same support as used in Example 10 to prepare a drug-containing medical adhesive sheet.

EXAMPLE 12

A drug-containing medical adhesive sheet was prepared in the same manner as in Example 10, except for replacing aluminum tris(acetylacetonate) as a crosslinking agent with 1.5 parts of dipropoxybis(acetylacetonato)titanium.

EXAMPLE 13

A drug-containing medical adhesive sheet was prepared in the same manner as in Example 11, except for replacing isopropyl myristate as an organic liquid component with 40 parts of diethyl sebacate.

EXAMPLE 14

A drug-containing medical adhesive sheet was prepared in the same manner as in Example 10, except for changing the solid content of the acrylic polymer and the amount of isopropyl myristate to 40 parts and 50 parts, respectively.

EXAMPLE 15

A drug-containing medical adhesive sheet was prepared in the same manner as in Example 11, except for replacing the isopropyl myristate as an organic liquid component with a combination of 25 parts of isopropyl myristate and 15 parts of diethyl sebacate.

EXAMPLE 16

A drug-containing medical adhesive sheet was prepared in the same manner as in Example 10, except for changing the solid content of the acrylic polymer and the amount of isopropyl myristate to 40 parts and 45 parts, respectively, and replacing 10 parts of Bunitrolol with 15 parts of Bunitrolol hydrochloride.

COMPARATIVE EXAMPLE 11

A drug-containing medical adhesive sheet was prepared in the same manner as in Example 10, except that the coating solution was prepared from 90 parts of the solid content of the acrylic polymer and 10 parts of Bunitrolol and the crosslinking agent was not added. In this case, the pressure-sensitive adhesive layer did not contain the organic liquid component and was not crosslinked.

COMPARATIVE EXAMPLE 12

A drug-containing medical adhesive sheet, in which the pressure-sensitive adhesive layer thereof did not contain the organic liquid component and was not crosslinked, was prepared in the same manner as in Comparative Example 11, except that the coating solution was prepared from 85 parts of the solid content of the acrylic polymer and 15 parts of Bunitrolol.

COMPARATIVE EXAMPLE 13

The same coating solution as prepared in Example 10 was applied to a 25 μm thick, non-porous polyester film and dried to form a crosslinked pressure-sensitive adhesive layer having a dry thickness of 80 μm.

A 75 μm thick polyester separator was laminated on the pressure-sensitive adhesive layer to prepare a drug-containing medical adhesive sheet.

COMPARATIVE EXAMPLE 14

The same coating solution as prepared in Example 10 was applied to a 75 μm thick polyester separator and dried to form a crosslinked pressure-sensitive adhesive layer having a dry thickness of 80 μm.

The resulting pressure-sensitive adhesive layer was adhered to the non-woven fabric side of the same support as used in Example 10 to prepare a drug-containing medical adhesive sheet.

COMPARATIVE EXAMPLE 15

A drug-containing medical adhesive sheet was prepared in the same manner as in Comparative Example 14, except for adding 1.5 parts of acetoacetonatotitanium to 100 parts of the solid content of the acrylic polymer.

COMPARATIVE EXAMPLE 16

A drug-containing medical adhesive sheet was prepared in the same manner as in Comparative Example 14, except for replacing isopropyl myristate as an organic liquid component with diethyl sebacate.

COMPARATIVE EXAMPLE 17

A drug-containing medical adhesive sheet was prepared in the same manner as in Comparative Example 14, except for changing the amounts of the acrylic polymer and isopropyl myristate to 40 parts and 50 parts, respectively.

COMPARATIVE EXAMPLE 18

A drug-containing medical adhesive sheet was prepared in the same manner as in Comparative Example 14, except for replacing the isopropyl myristate as an organic liquid component with a combination of 25 parts of isopropyl myristate and 15 parts of diethyl sebacate.

Each of the drug-containing medical adhesive sheets obtained in Examples 10 to 16 and Comparative Examples 11 to 18 was evaluated in the same manner as described above. The results obtained are shown in Table 2 below.

TABLE 2

| Example No. | Remaining of Adhesive | Drug Migration Weight (μg) | Peel Strength of Embedded Adhesive Layer (g/24 mm width) |
|---|---|---|---|
| Example 10 | none | 1160 ± 230 | 16 |
| Example 11 | none | 1560 ± 170 | 12 |
| Example 12 | none | 1125 ± 185 | 15 |
| Example 13 | none | 1112 ± 126 | 10 |
| Example 14 | none | 1424 ± 196 | 18 |
| Example 15 | none | 1530 ± 244 | 12 |
| Example 16 | none | 1018 ± 136 | 14 |
| Comparative Example 11 | none | 615 ± 158 | — |
| Comparative Example 12 | none | 910 ± 360 | — |
| Comparative Example 13 | observed | unmeasurable due to adhesive remaining | — |
| Comparative Example 14 | observed due to adhesive remaining | unmeasurable | 1 |
| Comparative Example 15 | observed due to adhesive remaining | unmeasurable | 1 |
| Comparative Example 16 | observed due to adhesive remaining | unmeasurable | 1 |
| Comparative Example 17 | observed due to adhesive remaining | unmeasurable | 2 |
| Comparative Example 18 | observed due to adhesive remaining | unmeasurable | 2 |

As is apparent from the results in Table 2, the drug-containing medical adhesive sheet according to the present invention exhibits moderate adhesion to the skin as well as satisfactory anchoring property. Further, the pressure-sensitive adhesive sheet shows sufficient migration of Bunitrolol, a drug for percutaneous absorption having a systemic action, to the skin, proving practical for percutaneous administration of the drug. Compared with the samples of Examples 10 to 16, the samples of Comparative Examples 11 and 12, in which the pressure-sensitive adhesive layer is not crosslinked, are inferior in drug migration to the skin, and the samples of Comparative Examples 14 to 18 are likely to turn out unsatisfactory for practical use in terms of anchoring property and adhesive remaining because of insufficient embedment of the pressure-sensitive adhesive layer in the porous sheet.

While the invention has been described in detail and with reference to specific examples thereof, it will be apparent to one skilled in the art that various changes and modifications can be made therein without departing from the spirit and scope thereof.

What is claimed is:

1. A direct coating method for preparing a medical adhesive sheet comprising the steps of:
   providing a porous sheet having a basis weight of 5 to 30 g/m² selected from the group consisting of sheets obtained by subjecting non-porous sheets to perforation or expansion to form open cells, papers, woven fabrics, nonwoven fabrics and knitted fabrics;
   forming a support having a laminate structure comprising a non-porous sheet and the porous sheet;
   preparing a pressure-sensitive adhesive solution which comprises an acrylic polymer prepared by polymerizing and crosslinking an alkyl (meth)acrylate as a main monomer component and an organic liquid component which is compatible with the acrylic polymer, wherein said organic liquid is present in an amount of from 25 to 200 parts by weight per 100 parts by weight of the acrylic polymer,
   applying the pressure-sensitive adhesive solution directly onto the porous sheet of the support, and
   drying the pressure-sensitive adhesive solution to form a crosslinked pressure-sensitive adhesive layer which reaches the laminate interface between the non-porous sheet and the porous sheet.

2. The direct coating method according to claim 1, wherein said acrylic polymer is a copolymer obtained from an alkyl (meth)acrylate having from 4 to 18 carbon atoms in the alkyl moiety thereof and at least one copolymerizable monomer selected from the group consisting of a polar monomer and a vinyl monomer.

3. The direct coating method according to claim 2, wherein said copolymerizable polar monomer is at least one compound selected from the group consisting of a carboxyl-containing monomer, a hydroxyl-containing monomer, an amido-containing monomer, an alkoxy-containing monomer, and a monomer containing an oxido bond in the side chain thereof.

4. The direct coating method according to claim 3, wherein said polar monomer is at least one compound selected from the group consisting of a (meth)acrylic acid, a hydroxyalkyl (meth)acrylate, a (meth)acrylamide, and an alkoxyalkyl (meth)acrylate.

5. The direct coating method according to claim 2, wherein said vinyl monomer is at least one compound selected from the group consisting of a vinyl acetate, a vinyl propionate, and a N-vinyl-2-pyrrolidone.

6. The direct coating method according to claim 1, wherein said organic liquid component is at least one compound selected from the group consisting of alcohols, glycols, fats and oils, organic solvents, long chain fatty acids, long chain fatty acid monoalkyl esters, long chain fatty acid dialkyl esters, and surface active agents.

7. The direct coating method according to claim 1, wherein said organic liquid component is present in an amount of from 40 to 180 parts by weight per 100 parts by weight of said acrylic polymer.

8. The direct coating method according to claim 7, wherein said organic liquid component is present in an amount of from 60 to 180 parts by weight per 100 parts by weight of said acrylic polymer.

9. The direct coating method according to claim 1, wherein said crosslinking is carried out by adding a crosslinking agent or copolymerizing a polyfunctional monomer.

10. The direct coating method according to claim 9, wherein said crosslinking agent is at least one compound selected from the group consisting of a metal alcoholate, a metal chelate compound, and a polyfunctional isocyanate.

11. The direct coating method according to claim 1, wherein said non-porous, sheet is a plastic sheet, a metal foil, a metal-deposited plastic sheet, or a laminate sheet composed of a plastic sheet and a metal foil.

12. The direct coating method according to claim 1, wherein said non-porous sheet has a thickness of from 1 to 25 $\mu$m.

13. The direct coating method according to claim 1, wherein said porous sheet is a paper, a woven fabric, a nonwoven fabric, a knitted fabric or a combination thereof.

14. The direct coating method according to claim 1, wherein said laminate sheet comprising a non-porous sheet and a porous sheet is prepared by laminating the non-porous sheet and the porous sheet via an adhesive.

15. The direct coating method according to claim 1, wherein said pressure-sensitive adhesive layer further comprises a drug for percutaneous absorption.

16. The direct coating method according to claim 15, wherein said drug has a systemic action.

* * * * *